US005744114A

United States Patent [19]

Persello

[11] Patent Number: 5,744,114
[45] Date of Patent: Apr. 28, 1998

[54] METHOD OF PREPARING DENTIFRICE-COMPATIBLE SILICA PARTICULATES

[75] Inventor: Jacques Persello, Montluel, France

[73] Assignee: Rhone-Poulenc Chimie, Courbevoie Cedex, France

[21] Appl. No.: 682,332

[22] Filed: Jul. 16, 1996

Related U.S. Application Data

[60] Continuation of Ser. No. 784,994, Oct. 30, 1991, abandoned, which is a division of Ser. No. 261,935, Oct. 25, 1988, abandoned.

[30] Foreign Application Priority Data

Nov. 4, 1987 [FR] France ................................. 87 15276

[51] Int. Cl.$^6$ ........................................... C01B 33/12
[52] U.S. Cl. .................... 423/335; 423/338; 423/339
[58] Field of Search .............................. 423/335, 338, 423/339; 424/49

[56] References Cited

U.S. PATENT DOCUMENTS

| | | | |
|---|---|---|---|
| 3,794,712 | 2/1974 | Aboutbout et al. | 423/339 |
| 3,800,031 | 3/1974 | Sale et al. | 423/338 |
| 3,803,046 | 4/1974 | Winyall et al. | 252/317 |
| 4,049,781 | 9/1977 | Acker et al. | 423/338 |
| 4,216,113 | 8/1980 | Winyall | 252/317 |
| 4,676,964 | 6/1987 | Seki et al. | 423/335 |
| 4,678,652 | 7/1987 | Tamenori et al. | |
| 4,973,462 | 11/1990 | Akira et al. | 423/339 |

OTHER PUBLICATIONS

Green & Maloney (eds). "Perry's Chemical Engineers' Handbook", 6th Ed., McGraw-Hill, New York, NY, pp. 18.1–18.3, 18.50 (1984).

S.K. Wason, "Cosmetic Properties and Structure of Fine-Particle Synthetic Precipitated Silicas," J. Soc. Chem., 29, 497–521 (Aug. 1978).

Primary Examiner—George R. Fourson
Attorney, Agent, or Firm—Burns, Doane, Swecker & Mathis, L.L.P.

[57] ABSTRACT

Novel silica particulates adopted for formulation into dentifrice compositions have a unique surface chemistry as to be at least 50% compatible with zinc values, and have a number of OH functions, expressed as OH/nm$^2$, of at most 15 and a zero charge point (PZC) of from 3 to 6.5.

22 Claims, No Drawings

METHOD OF PREPARING DENTIFRICE-COMPATIBLE SILICA PARTICULATES

CROSS-REFERENCE TO COMPANION APPLICATION

This application is a continuation of application Ser. No. 07/784,994, filed Oct. 30, 1991, a divisional of application Ser. No. 07/261,935, filed Oct. 25, 1988, both now abandoned. My copending application, Ser. No. 07/261,936, filed concurrently herewith and assigned to the assignee hereof.

BACKGROUND OF THE INVENTION

1. Field of the Invention

The present invention relates to novel silica particulates especially well adopted for incorporation into dentifrice compositions, to a process for the production of such novel particulates, and to improved dentifrice compositions comprising same.

2. Description of the Prior Art

It is known to this art that silica is a useful material for incorporation into dentifrice compositions. It performs a variety of different functions therein.

Firstly, it serves as an abrasive agent, thus mechanically contributing to the elimination of dental plaque.

It may also serve as a thickening agent to impart particular rheological properties to the dentifrice, as well as a colorant to impart particular coloration to the composition.

It is also known to this art that dentifrices contain various active agents, in particular for the prevention of dental caries, to reduce the formation of dental plaque or the deposition of tartar on the teeth. Among such agents, the zinc compounds are especially representative. Other elements are also incorporated, such as fluorides, phosphates, the pyrophosphates, polyphosphates, polyphosphonates, guanidines, in particular the bis-biguanides, and one of the compounds most typically included is chlorhexidine. Dentifrice formulations may also contain flavorants, perfumes, and the like.

The presence of these agents in the dentifrice presents the problem of their compatibility with silica. In effect, due particularly to its absorbent properties, the latter may have a tendency to react with these agents such that they are no longer available to elicit their aforesaid therapeutic and/or useful responses.

SUMMARY OF THE INVENTION

Accordingly, a major object of the present invention is the provision of a novel silica material that is improvedly compatible with the typical dentifrice additives, in particular the zinc compounds, as well as a process for the preparation of such improvedly compatible silica particulates.

It has now unexpectedly been determined that the desired compatibility essentially depends on the surface chemistry of the silica particles. Indeed, it has now been established that there must exist a certain number of surface conditions in order that the silica particles will be compatible.

The silica particulates according to the present invention are characterized in that they display compatibility with zinc compounds of at least 50%, and have a number of OH functions, expressed as $OH/nm^2$, of at most 15 and a zero charge point (PZC) ranging from 3 to 6.5.

In a process embodiment of this invention, the novel silica particulates are prepared by reacting a silicate with an acid, whereby a suspension or gel of the silica is produced, then separating and drying the silica, and thereafter washing the separated silica cake with water, followed by a second washing or a treatment with an acid solution.

Another object of the present invention is the provision of improved dentifrice compositions comprising silica particulates of the above type, or prepared by the aforesaid process embodiment.

DETAILED DESCRIPTION OF THE PREFERRED EMBODIMENTS OF THE INVENTION

More particularly according to the present invention, as indicated above, the essential characterizing features of the subject novel silica particulates reside in the surface chemistry thereof. Thus, surface acidity is an important aspect. Relative to such acidity, one of the distinguishing characteristics of the silica particulates of the invention is the number of their surface acid sites.

This number may be measured as the number of OH or silanol groups per $nm^2$.

Such number is determined as follows:

The number of OH sites on the surface is associated with the amount of water released by silica at temperatures of 190° C. and 900° C.

The silica specimens are initially dried at 105° C. for 2 hours.

A mass Po of silica is placed in a thermobalance and heated to 190° C. for 2 hours; the mass obtained is P190. The silica is then heated to 900° C. for 2 hours; the new mass obtained is P900.

The number of OH sites is calculated by the following equation:

$$NOH = \frac{66922.2}{A} \times \frac{P190 - P900}{P190}$$

wherein NOH is the number of OH sites per $nm^2$ of the surface, and A is the (BET) specific surface of the solid, in $m^2/g$.

In the present case, the silica particulates of the invention advantageously have a number of $OH/nm^2$ less than or equal to 15, more particularly a maximum of 12, and preferably ranging from 3 to 12.

The nature of the OH sites of the silica particulates of the invention, which is also a characteristic of their surface chemistry (pH of the surface), too may be determined by the point of zero charge.

The point of zero charge (PZC) is defined by the pH of a suspension of silica for which the electrical charge of the surface of the solids is zero, regardless of the ionic strength of the medium. This PZC measures the real pH of the surface, to the extent that it is free of impurities of the ionic type.

The electrical charge is determined by potentiometry. The principle of the method is based on the total balance of protons adsorbed or desorbed on the surface of the silica at a given pH.

By means of the equations describing the total balance of the operation, it is easy to show that the electrical charge C of the surface, considered relative to a corresponding reference, has a zero surface charge given by the equation:

$$C = \frac{F}{A \cdot M} (H-OH)$$

wherein:

A is the specific surface of the solids, in m²/g;
M is the amount of solids in the suspension, in g;
F is the Faraday constant;
H or OH represents the variation per unit of the surface of the excess of H⁺ or OH⁻ ions, respectively, of the solids.

The experimental procedure of the determination of PZC is the following:

The method described by Berube and Bruyn, *J. Colloid Interface Sc.*, 27, 305 (1968) is used.

The silica is initially washed in high resistivity deionized water (10 Mega.Ohm.cm), dried and degassed.

In actual practice, a series of solutions at pHo 8.5 is prepared by the addition of KOH or $HNO_3$ and containing an electrolyte ($KNO_3$) in a concentration of from $10^{-5}$ to $10^{-1}$ mole/l.

To these solutions, a given mass of silica is added and the pH of the resulting suspensions is permitted to stabilize under agitation, at 25° C. and under nitrogen, for 24 h; its value is the pH'o.

The standard solutions are the supernatants obtained by centrifugation for 30 min at 1.000 rpm of a fraction of the same suspensions; the pH'o is the pH of these supernatants.

The pH of a known volume of these suspensions and of corresponding standard solutions is adjusted to pHo by adding the necessary amount of KOH and the suspensions and standard solutions are permitted to stabilize for 4 hours.

Voh.Noh is the number of equivalents of base added to change from the pH'o to pHo of a known volume (V) of the suspension of the standard solution.

The potentiometric analysis of the suspensions and the standard solutions is carried out from the pHo by the addition of nitric acid to a pHf=2.0.

Preferably, acid is added incrementally corresponding to a variation of the pH by 0.2 pH units. After each addition, the pH is stabilized to attain pHf.

Beginning with pHo, the (Vh.Nh−Voh.Noh) is plotted as a function of the pH increments for all of the suspensions (at least 3 ionic strengths) and for all of the corresponding standard solutions.

For each value of pH (no 0.2 unit), the difference between the consumption of H⁺ or OH⁻ for the suspension and the corresponding standard solution is then established. This operation is repeated for all ionic strengths.

This gives the (H—OH) corresponding to the consumption of the protons of the surface. The surface charge is calculated by the above equation.

Subsequently, the curves of the surface charge are calculated as a function of the pH for all of the ionic strengths considered. The PZC is defined by the intersection of the curves.

The silica concentration is then adjusted as a function of its specific surface.

For example, 2% suspensions are used for 50 m²/g silica at 3 ionic strengths (0.1, 0.01 and 0.001 mole/l).

100 ml of the suspension are analyzed by using 0.1 M potassium hydroxide.

The PZC of the silica particulates of the present invention ranges from 3 to 6.5.

To further improve compatibility, in particular relative to elements other than zinc, in particular fluorine, it is advantageous to limit the aluminum content of the silica of the invention to a maximum of 500 ppm.

The maximum iron content of the silica of the invention should be 200 ppm.

The maximum calcium content may be 500 ppm and more particularly 300 ppm.

The silica of the invention preferably has a maximum carbon content of 50 ppm and more particularly of 10 ppm.

The pH of the silica according to the invention measured by the NFT (French National Standard) standard 45-007 is generally at most 7. More particularly, it ranges from 5.5 to 7, and preferably from 6.0 to 7.0.

These characteristics make it possible to obtain silica particulates that are compatible with zinc compounds. This compatibility, measured by the test described below, is at least 50%, preferably at least 80%, and more preferably at least 90%. Depending upon the particular case, the silica particulates of the invention are also compatible with fluorides, phosphates and derivatives thereof.

In addition to the chemical surface properties described above, which impart compatibility thereto, the silica particulates of the invention have physical properties which are perfectly suited for their use in dentifrices. These structural characteristics are described as follows.

Advantageously, the BET surface of the silica particulates of the invention ranges from 40 to 600 m²/g, and more preferably from 40 to 350 m²/g. Their CTAB surface typically ranges from 4 to 400 m²/g, and more preferably from 40 to 200 m²/g.

The BET surface is determined by the BRUNAUER-EMMET-TELLER method described in the *Journal of the American Chemical Society*, Vo. 60, p. 309 (February 1938) and according to the standard NF X11-622 (3.3).

The CTAB surface is the external surface determined by the ASTM standard D3785, but by using the adsorption of hexadecyltrimethyl ammonium bromide (CTAB) at pH 9 and taking 35 Å°² as the projected area of the CTAB molecule.

The silica of the invention may correspond to the three types usually distinguished in the dentifrice field.

Thus, the silica particles of the invention may be of the abrasive type. Same then have a BET surface of from 40 to 300 m²/g. In this case, the CTAB surface ranges from 40 to 100 m²/g.

The silica particles of the invention may also be of the thickening type. Their BET surface then ranges from 120 to 450 m²/g, and more preferably from 120 to 200 m²/g. They may have a CTAB surface of from 120 to 400 m²/g, and more preferably from 120 to 200 m²/g.

Finally, as a third type, the silica particles of the invention may be bifunctional. In this instance they have a BET surface of from 80 to 200 m²/g. Their CTAB surface ranges from 80 to 200 m²/g.

The silica particles of the invention may also exhibit an oil uptake of from 80 to 500 cm³/100 g determined by the NFT standard 30-022 (March 53) using dibutyl phthalate.

More precisely, such oil uptake ranges from 100 to 140 cm³/100 g for the abrasive silica, from 200 to 400 for the thickening silica and from 100 to 300 for the bifunctionals.

The silica particulates preferably have, again vis-a-vis their dentifrice applications, a particle size of from 1 to 10 µm.

This mean particle size is measured by Counter-Coulter.

The apparent density thereof generally ranges from 0.01 to 0.3. In a preferred embodiment of the invention, the silica particulates are precipitated silica particulates.

Finally, the silica of the invention has a refraction index generally from 1.440 to 1.465.

The process for the preparation of the silica of the invention will now be described in greater detail.

As indicated above, the process is of the type comprising reacting a silicate with an acid, resulting in the formation of a suspension or gel of silica.

It will be appreciated that any known operation may be used to prepare this suspension or gel (addition of acid to the base of a vat of silica, simultaneous total or partial addition of the acid and the silicate to the base of a water vat, or a solution of silicate, etc.), with the selection being made essentially as a function of the physical characteristics of the silica to be produced. It may be advantageous to adjust the pH of the resulting suspension or gel to a value of at most 6 and preferably ranging from 4 to 6.

The silica is then separated from the reaction medium by any known means, for example vacuum filtration or filter press.

A silica filter cake is recovered.

In a primary characteristic of the invention, this filter cake is subjected to a first washing with water, advantageously with deionized water.

The silica particulates are next subjected to a second washing with water, or are treated with an acid solution.

The purpose of the second wash, or acid treatment, is to provide silica particulates having a pH of at most 7, preferably a pH ranging from 5.5 to 7, and more preferably a pH ranging from 6.0 to 7.0, as well as a PZC ranging from 3 to 6.5.

The acid solution may be, for example, a solution of an inorganic acid, such as nitric acid.

However, in a preferred embodiment of the invention, the acid solution may also be a solution of an organic acid, in particular a complexing organic acid. Such an acid is advantageously selected from among carboxylic, dicarboxylic, hydroxycarboxylic and aminocarboxylic acids.

Exemplary of such acids is acetic acid, and exemplary of the complexing acids are tartaric, maleic, glyceric, gluconic and citric acids.

The second wash, or the treatment with acid, may be carried out by pouring the acid solution over the filter cake, or introducing it into the suspension obtained by the comminution or grinding of the cake. Such wash or acid treatment is conducted under conditions as to provide silica particulates having the aforesaid final pH value; the pH of the suspension or medium, prior to drying, must range from 4 to 6, and preferably from 5 to 6.

It may be advantageous, especially in the case in which a solution of a mineral acid is used, to conduct a final wash with deionized water.

In another embodiment of the invention, following the acid/silicate reaction and immediately before the separation of the silica, the suspension or gel is aged. This aging is typically carried out at a maximum pH of 6, for example, at a value of from 4 to 6.

It is also possible to carry out the aging during the reaction, for example at a pH of from 6 to 8. The aging is preferably conducted at an elevated temperature, for example a temperature of from 80° C. to 100° C., and for a period of time ranging from fifteen minutes to two hours.

After the cake is washed and treated as described above, the cake, or if it is comminuted, the suspension is dried by any known means. In particular, drying is by atomization. The dried product is ground, if necessary, to obtain the grain size distribution desired.

This invention also features improved dentifrice compositions containing the above novel silica particulates, advantageously prepared by the aforesaid distinct processes.

The amount of silica incorporated into such improved dentifrice compositions may vary over wide limits, but typically it ranges from 5 to 35% by weight.

The silica particulates of the invention are well adopted for incorporation into dentifrice compositions comprising at least one element selected from among the fluorides, phosphates, and zinc.

As regards the fluoride compounds, the amount thereof preferably corresponds to a fluorine concentration in the ultimate composition of from 0.01 to 1% by weight, notably from 0.1 to 0.5% by weight. The preferred fluoride compounds are the salts of monofluorophosphoric acid, and in particular those of sodium, potassium, lithium, calcium, aluminum and ammonium, mono- and difluorophosphate, as well as the various fluorides containing fluorine in the form of a bonded ion, particularly alkaline fluorides, such as those of sodium, potassium, lithium, ammonium fluoride, stannous fluoride, manganese fluoride, zirconium fluoride, aluminum fluoride, together with addition products of these fluorides with each other or with other fluorides, such as potassium, sodium or manganese fluorides.

Other fluorides may also be incorporated in the dentifrices of the present invention, such as, for example, zinc fluoride, germanium fluoride, palladium and titanium fluorides, and alkaline fluozirconates, such as, for example, of sodium or potassium, stannous fluozirconate, and sodium or potassium fluoborate or fluosulfates.

Organic fluorine compounds may also be incorporated, preferably known compounds such as the addition products of amines and long chain amino acids with hydrogen fluoride, cetylamine fluoride, the dihydrofluoride or bis-(hydroxyethyl)aminopropyl-N-hydroxyethyl octadecylamine, octadecylamine fluoride and the dihydrofluoride of N,N',N'tri-(polyoxyethylene)-N-hexadecylpropylenediamine.

Zinc is incorporated, in particular, in the form of its citrate or sulfate.

As elements that are useful as anti-plaque agents of the polyphosphate or polyphosphonate, guanidine, or bis-biguanide type, those set forth in U.S. Pat. Nos. 3,934,002 and 4,110,083 are representative.

The subject dentifrice compositions may also comprise a binder.

The principal binders are selected from among:
(i) Cellulose derivatives: methylcellulose, hydroxyethyl cellulose, sodium carboxymethylcellulose;
(ii) Mucilages: carraghenates, alginates, agar-agar and geloses;
(iii) Gums: arabic and tragacanth gums, xanthan gum, Karaya gum;
(iv) Carboxyinvyl and acrylic polymers;
(v) Polyoxyethylene resins.

In addition to the silica particulates of the invention, the dentifrice compositions may contain one or more other abrasive polishing agents selected from among:
(i) Precipitated calcium carbonate;
(ii) Magnesium carbonate;
(iii) Di- and tricalcium phosphates;
(iv) Insoluble sodium metaphosphate;
(v) Calcium pyrophosphate;
(vi) Titanium dioxide (whitening agent);
(vii) Silicates;
(viii) Alumina and silicoaluminates;
(ix) Zinc and tin oxides;
(x) Talc;
(xi) Kaolin.

These dentifrice compositions may also contain detergents, humectants, aromatics, sweeteners and colorants and preservatives.

The principal detergents are selected from among:
(i) Sodium laurylsulfate;
(ii) Sodium laurylether sulfate and laurylsulfoacetate;

7

(iii) Sodium dioctylsulfosuccinate;
(iv) Sodium laurylsarcosinate;
(v) Sodium ricinoleate;
(vi) Monoglycerine sulfates.

The principal humectants are selected from among the polyalcohols, such as:

(i) Glycerol;
(ii) Sorbitol, generally in a 70% solution in water;
(iii) Propylene glycol.

The principal aromatics are selected from among: essences of anise, chinese anise, mint, juniper berry, cinnamon, cloves and roses.

The principal sweetening agents are orthosulfobenzoic imides and cyclamates.

The principal colorants are those selected from among:

(i) Red and rose colorants: amaranth, azorubin, catechou, new coccine (PONCEAU 4 R), cochineal, erythrosine;
(ii) Green colorants: chlorophyll and chlorphylline;
(iii) Yellow colorants: sun yellow (Orange S) and quinoline yellow.

The principal preservatives are: parahydroxybenzoates, formaldehyde and products releasing same, hexetidine, quaternary ammonium compounds, hexachlorophene, bromophene and hexamedine.

Finally, the dentifrice compositions may contain therapeutic agents, principally selected from among:

(i) Antiseptics and antibiotics;
(ii) Enzymes;
(iii) Oligoelements and the fluorine compounds described above.

In order to further illustrate the present invention and the advantages thereof, the following specific examples are given, it being understood that same are intended only as illustrative and in nowise limitative.

In said examples to follow, the tests described immediately below were carried out to measure the compatibility of the silica with various compounds.

% Compatibility =

$$\frac{\text{absorbance of test solution}}{\text{absorbance of reference solution}} \times 100$$

Measurement of compatibility with fluorides:

4 g silica were dispersed in 16 g of a 0.3% solution of sodium fluoride (NaF). The suspension was agitated for 24 h at 37° C. After centrifugation at 20,000 rpm for 30 min, the supernatant was filtered on a 0.2 μm Millipore filter. The solution obtained in this manner constituted the test solution.

A reference solution was prepared by the same procedure, but without the silica.

The compatibility with fluorides was determined by the % of free fluoride measured by a fluoride selective electrode (Orion).

It was determined by the following relationship:

$$\% \text{ Compatibility} = \frac{\text{Concentration in } F \text{ of the test solution (ppm)}}{\text{Concentration in } F \text{ of the reference solution (ppm)}} \times 100$$

Measurement of compatibility with zinc:

4 g silica were dispersed in 100 ml of a 0.06% aqueous solution of $ZnSO_4 \cdot 7 H_2O$. A suspension was obtained, the pH of which was stabilized at 7 in 15 min by the addition of NaOH or $H_2SO_4$. The suspension was then agitated for 24 h at 37° C. and centrifuged at 20,000 rpm for 30 min.

The supernatant, filtered on a 0.2μm Millipore filter, constituted the test solution.

8

A reference solution was prepared by the same procedure, but without the silica.

The concentration of free zinc in the two solutions was determined by atomic absorption (214 nm).

The compatibility was determined by the following relationship:

$$\% \text{ Compatibility} = \frac{\text{Concentration of Zn in the test solution (ppm)}}{\text{Concentration of Zn in the reference solution (ppm)}} \times 100$$

Measurement of compatibility with sodium and potassium pyrophosphates:

4 g silica were dispersed in 16 g of a 1.5% aqueous suspension of sodium or potassium pyrophosphate. The suspension was agitated for 24 h at 37° C., then centrifuged at 20,000 rpm for 30 min.

The supernatant was filtered on a 0.2 μm Millipore filter. 0.2 g of the solution, diluted in 100 ml water in a volumetric flask, constituted the test solution.

A reference solution was prepared by the same procedure, but without the silica.

The free pyrophosphate ion ($P_2O_7^=$) concentration of the two solutions was determined by ionic chromatography (DIONEX 2000i system), equipped with an integrator.

The compatibility was determined from the areas of the peaks obtained in the chromatograms and corresponding to the retention time of the pyrophosphate in the test and reference solutions.

$$\% \text{ Compatibility} = \frac{\text{Area of the peak of the test solultion}}{\text{Area of the peak of the reference solultion}} \times 100$$

EXAMPLE 1

Into a reactor equipped with a temperature and pH control system and a turbine agitation system, 6 l of deionized water were introduced.

After commencing agitation (300 rpm), the contents of the reactor were heated to 85° C.

When this temperature was reached, the following materials were simultaneously added: 8.5 l sodium silicate having a silica concentration of 120 g/l and a $SiO_2/Na_2O$ ratio of 3.5, at a flow rate of 0.34 l/min, and 13.5 l sulfuric acid having a concentration of 80 g/l. The acid flow rate was adjusted such that the pH of the medium was maintained at a constant value 8.0.

After 40 min of addition, the mixture was aged for 10 min at this pH and temperature.

The addition of the silicate was discontinued and the addition of the acid continued until the pH of the reaction mixture was stabilized at 4.

The mixture was then aged for 15 min at this pH and at 85° C.

It was subsequently filtered and the moist filter cake was washed with deionized water.

The filter cake was then dispersed in deionized water to form a homogeneous suspension having a silica concentration of 50 g/l. The pH of this suspension was adjusted to 5.8 by the addition of nitric acid and it was permitted to stabilize at this pH for 15 min.

The suspension was filtered.

The product was then dried by atomization and ground in a forplex type grinder to produce a grain size of 9 microns.

The physico/chemical properties of the resulting silica particulates were as follows:

| | | |
|---|---|---|
| (i) | BET surface | 90 m²/g |
| (ii) | CTAB surface | 66 m²/g |
| (iii) | Oil uptake | 105 cm³/100 g |
| (iv) | pH | 6.8 |
| (v) | Number of OH/nm² | 8. |

The chemical analyses of the silica are reported in the following table:

| Ions | Al | Fe | Ca | C |
|---|---|---|---|---|
| ppm | 350 | 110 | 300 | 10 |

The PZC of the silica was 4.5.

In the following table the different compatibilities of the silica particles with the various ingredients of a dentifrice formulation and measured by the different tests described above, are set forth:

| Ingredients | Fluoride (NaF) | Pyrophosphate (Na/K) | Zinc (ZnSO₄) |
|---|---|---|---|
| % Compatibility | 90 | 98 | 90 |

COMPARATIVE EXAMPLE 2

As a comparison, compatibility measurements were made using the commercial silica typically employed in dentifrice formulations, and these are reported below, together with the physico/chemical properties thereof:

| Silica (trademark of manufacturer) | Surfaces (m²/g) CTAB | BET | Number OH/nm² | Compatibilities Zn | F | Pyrophosphate |
|---|---|---|---|---|---|---|
| Zeodent (Hubert) | 50 | 100 | 30 | 0 | 95 | 95 |
| Tixosil 53 (Rhone-Poulenc) | 50 | 250 | 30 | 0 | 60 | 90 |
| Z 119 (Rhone-Poulenc) | 50 | 60 | 25 | 20 | 95 | 95 |

It should be noted that for the silica of this table the PZC was less than 3.

EXAMPLE 3

This example relates to the formulation of an opaque dentifrice of the paste type:

Its formula was the following:

| | |
|---|---|
| Glycerin | 22.00 |
| CMC 7mFD | 1.00 |
| Sodium saccharinate | 0.20 |
| Sodium monofluorophosphate | 0.76 |
| Sodium fluoride | 0.10 |
| Sodium lauryl sulfate (30% aqueous) | 4.67 |
| Sodium benzoate | 0.10 |
| Perfume | 0.90 |
| Titanium dioxide | 1.00 |
| Silica of Example 1 | 31.50 |

-continued

| | |
|---|---|
| ZnSO₄ · 7 H₂O | 0.48 |
| Distilled water | 37.29 |

Rheological testing and visual examination of the above paste dentifrice evidenced that the conventional properties thereof were good.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of silica particulates adapted for formulation into dentifrice compositions, having a surface chemistry as to be at least 50% compatible with zinc values, and having a number of OH functions, expressed as OH/nm² of at most 15 and a zero charge point of from 3 to 6.5, the process comprising steps of reacting a silicate with an acid to form a suspension or gel of silica, separating silica particulates from said suspension or gel, first washing said silica particulates with water and then conducting an acid treatment by washing said silica particulates with an inorganic acid solution until said silica particulates have a pH≦7 followed by drying said silica particulates, the pH of the silica suspension or gel being adjusted to a value of at most 6 prior to the first washing step.

2. The process as defined by claim 1, comprising aging the suspension or gel or silica prior to the separation thereof.

3. The process as defined by claim 1, comprising adjusting the pH of the silica suspension or gel to a value of from 4 to 6.

4. The process as defined by claim 1, wherein said silica particulates are dried by atomization during the drying step and the pH of the silica suspension or gel is lowered to a value no greater than 6 prior to the first washing step.

5. The process as defined by claim 1, further comprising washing the silica particulates with water after the acid treatment.

6. The process as defined by claim 1, further comprising forming a suspension of the silica particulates during the acid treatment and adjusting pH of said suspension to a value of at most 6 during the acid treatment and recovering silica particulates having a pH of ≦7 after the drying step.

7. The process as defined by claim 1, wherein the silica particulates are recovered in the form of a filter cake in the separating step and the filter cake is washed with deionized water during the first washing step.

8. The process as defined by claim 1, wherein the silica particulates are recovered in the form of a filter cake in the separating step and the filter cake is washed by pouring the acid solution over the filter cake during the acid treatment.

9. The process as defined by claim 1, wherein said acid treatment comprises washing said separated silica with a solution of a mineral acid.

10. The process as defined by claim 1, wherein said acid treatment comprises washing said separated silica with a solution of nitric acid.

11. The process as defined by claim 1, wherein the silica particulates have ≦500 ppm Al.

12. The process as defined by claim 1, wherein the silica particulates have ≦500 ppm Ca.

13. The process as defined by claim 1, wherein the silica particulates have ≦500 ppm Ca.

14. The process as defined by claim 1, wherein the silica particulates have ≦50 ppm C.

15. The process as defined by claim 1, wherein the silica particulates have a pH of 6–7.

16. The process as defined by claim 1, wherein the silica particulates have a BET surface area of 40–350 m$^2$/g.

17. The process as defined by claim 1, wherein the silica particulates have a CTAB surface area of 40–200 m$^2$/g.

18. The process as defined by claim 1, wherein the process includes adding the silica particulates to a dentifrice composition.

19. The process as defined by claim 1, wherein the silica particulates are washed with the inorganic acid solution until the silica particulates have a pH of 5.5 to 7.

20. The process as defined by claim 1, wherein the silica particulates are washed with the inorganic acid solution until the silica particulates have a pH of 6.0 to 7.0.

21. The process as defined by claim 1, wherein the silica particulates have a particle size of 1 to 10 μm.

22. The process as defined by claim 1, wherein the silica particulates have a refractive index of 1.440 to 1.465.

* * * * *